United States Patent
Lazzarini et al.

(10) Patent No.: US 10,376,934 B2
(45) Date of Patent: Aug. 13, 2019

(54) METHOD FOR CLEANING A MACHINE FOR LIQUID OR SEMI-LIQUID FOOD PRODUCTS

(71) Applicant: ALI S.p.A.—CARPIGIANI GROUP, Milan (IT)

(72) Inventors: Roberto Lazzarini, Reggio Emilia (IT); Andrea Cocchi, Calderara di Reno (IT)

(73) Assignee: ALI GROUP S.R.L.—CARPIGIANI, Cernuscosul (IT)

( * ) Notice: Subject to any disclaimer, the term of this patent is extended or adjusted under 35 U.S.C. 154(b) by 0 days.

(21) Appl. No.: 14/688,520

(22) Filed: Apr. 16, 2015

(65) Prior Publication Data
US 2015/0306640 A1 Oct. 29, 2015

(30) Foreign Application Priority Data
Apr. 24, 2014 (IT) .............................. BO2014A0236

(51) Int. Cl.
| | |
|---|---|
| A23G 9/30 | (2006.01) |
| B08B 9/08 | (2006.01) |
| A23G 9/28 | (2006.01) |
| A23G 9/08 | (2006.01) |
| A61L 2/04 | (2006.01) |

(52) U.S. Cl.
CPC .................. *B08B 9/08* (2013.01); *A23G 9/08* (2013.01); *A23G 9/28* (2013.01); *A23G 9/30* (2013.01); *A61L 2/04* (2013.01); *A61L 2202/17* (2013.01)

(58) Field of Classification Search
CPC ....................................................... A23G 9/30
See application file for complete search history.

(56) References Cited

U.S. PATENT DOCUMENTS

| | | | |
|---|---|---|---|
| 2,784,565 | A | 3/1957 | Stalkup et al. |
| 2,961,853 | A | 11/1960 | Cohrt et al. |

(Continued)

FOREIGN PATENT DOCUMENTS

| | | | |
|---|---|---|---|
| CN | 2621434 Y | 6/2004 | |
| CN | 1780785 A | 5/2006 | |

(Continued)

OTHER PUBLICATIONS

Italian Search Report dated Nov. 11, 2014 from counterpart app No. BO20140236.

(Continued)

*Primary Examiner* — Mikhail Kornakov
*Assistant Examiner* — Ryan L. Coleman
(74) *Attorney, Agent, or Firm* — Shuttleworth & Ingersoll, PLC; Timothy J. Klima

(57) ABSTRACT

A method for cleaning a machine for liquid or semi-liquid products, the machine includes:
  a first container intended to contain a liquid or semi-liquid basic mixture or finished product and also provided with related means for thermal treatment of the liquid or semi-liquid basic mixture or finished product and a mixer. The method includes, in time sequence, the following steps:
  a) emptying the basic mixture contained in the first container;
  b) washing said first container with a washing fluid;
  c) at least partly filling the first container with a cleaning fluid and subjecting the cleaning fluid in the first container to a pasteurizing thermal treatment.

5 Claims, 2 Drawing Sheets

(56) References Cited

U.S. PATENT DOCUMENTS

| | | | |
|---|---|---|---|
| 2,975,617 | A | 3/1961 | Wakeman et al. |
| 3,029,613 | A | 4/1962 | Lande et al. |
| 3,729,177 | A | 4/1973 | Keyes et al. |
| 3,811,494 | A | 5/1974 | Menzel |
| 3,829,242 | A | 8/1974 | Duke et al. |
| 3,898,859 | A | 8/1975 | Duke |
| 3,930,535 | A | 1/1976 | Menzel |
| 3,989,492 | A | 11/1976 | Keyes |
| 4,479,423 | A | 10/1984 | Schwitters et al. |
| 4,522,041 | A | 6/1985 | Menzel |
| 4,607,494 | A | 8/1986 | Cipelletti |
| 4,625,525 | A | 12/1986 | Bradbury et al. |
| 4,680,944 | A | 7/1987 | Menzel |
| 4,848,381 | A | 7/1989 | Livingston et al. |
| 4,860,550 | A | 8/1989 | Aoki et al. |
| 4,964,542 | A | 10/1990 | Smith |
| 5,016,446 | A | 5/1991 | Fiedler |
| 5,201,861 | A | 4/1993 | Menzel |
| 5,447,371 | A | 9/1995 | Agapiou |
| 5,615,559 | A | 4/1997 | Kress et al. |
| 5,692,392 | A | 12/1997 | Swier |
| 5,799,832 | A | 9/1998 | Mayo |
| 5,962,035 | A | 10/1999 | Masse et al. |
| 6,142,340 | A | 11/2000 | Watanabe et al. |
| 6,189,440 | B1 | 2/2001 | Amundson |
| 6,490,872 | B1 | 12/2002 | Beck et al. |
| 6,494,055 | B1 | 12/2002 | Meserole et al. |
| 7,640,755 | B1 | 1/2010 | Kateman |
| 7,681,761 | B2 | 3/2010 | Harra |
| 8,316,761 | B2 | 11/2012 | Bravo et al. |
| 8,758,678 | B2 | 6/2014 | Cocchi et al. |
| 9,402,408 | B2 | 8/2016 | Cocchi et al. |
| 9,693,571 | B2 | 7/2017 | Cocchi et al. |
| 2002/0162577 | A1* | 11/2002 | Cocchi ............... B60S 3/04 134/18 |
| 2004/0003620 | A1 | 1/2004 | Cocchi et al. |
| 2004/0251270 | A1 | 12/2004 | Davis et al. |
| 2005/0098575 | A1 | 5/2005 | Carhuff |
| 2005/0269362 | A1 | 12/2005 | Guerrero et al. |
| 2006/0024418 | A1 | 2/2006 | White et al. |
| 2006/0185755 | A1 | 8/2006 | Vaughn, Jr. |
| 2006/0240159 | A1* | 10/2006 | Cash ............... A23L 1/0155 426/392 |
| 2006/0243310 | A1 | 11/2006 | Cocchi et al. |
| 2006/0261086 | A1 | 11/2006 | Schroeder et al. |
| 2007/0102448 | A1* | 5/2007 | Harra ............... A23G 9/20 222/146.6 |
| 2007/0114228 | A1 | 5/2007 | Cocchi et al. |
| 2007/0275131 | A1 | 11/2007 | Bertini et al. |
| 2008/0295865 | A1* | 12/2008 | Ahn ............... A47L 15/0015 134/18 |
| 2010/0101235 | A1 | 4/2010 | Cocchi et al. |
| 2012/0251697 | A1 | 10/2012 | Cocchi et al. |
| 2013/0064034 | A1 | 3/2013 | Almblad et al. |
| 2013/0140328 | A1 | 6/2013 | Gates |
| 2014/0335232 | A1 | 11/2014 | Halachmi |
| 2015/0245634 | A1 | 9/2015 | Lazzarini et al. |

FOREIGN PATENT DOCUMENTS

| | | |
|---|---|---|
| CN | 101175412 A | 5/2008 |
| CN | 101263838 A | 9/2008 |
| CN | 101790319 A | 7/2010 |
| CN | 102726590 A | 10/2012 |
| EP | 0729707 A2 | 9/1996 |
| EP | 2279669 | 2/2011 |
| EP | 2491792 A1 | 8/2012 |
| JP | H02107160 A | 4/1990 |
| JP | H0690669 A | 4/1994 |
| JP | H06181732 A | 7/1994 |
| JP | 2001169729 A | 6/2001 |
| JP | 2002017268 A | 1/2002 |
| JP | 2006271221 A | 10/2006 |
| JP | 2006523459 A | 10/2006 |
| WO | 0121007 | 3/2001 |
| WO | 2004/091324 | 10/2004 |
| WO | 2009027757 A1 | 3/2009 |
| WO | 2014/003881 | 1/2014 |

OTHER PUBLICATIONS

Chinese Office Action dated Apr. 4, 2018 from counterpart Chinese App No. 201510312036.8.
Japanese Office Action dated Feb. 27, 2019 for counterpart Japanese Patent Application No. JP 2015-085788.
English translation of Japanese Office Action dated Feb. 7, 2019 for related Japanese Patent Application No. 2015085787.
Italian Search Report dated Nov. 11, 2014 from related Italian Application No. BO20140237.
International Search Report and Written Opinion dated Sep. 17, 2014 from related PCT Application No. PCT/IB2014/061586.

* cited by examiner

METHOD FOR CLEANING A MACHINE FOR LIQUID OR SEMI-LIQUID FOOD PRODUCTS

This application claims priority to Italian Patent Application No. BO2014A000236 filed Apr. 24, 2014, which application is incorporated by reference herein.

BACKGROUND OF THE INVENTION

This invention relates to a method for cleaning a machine for liquid or semi-liquid food products (designed to produce in particular products of the soft ice cream or shake type).

As is known, the components which are in contact with the basic mixture or with the finished product require regular cleaning, in order to reduce the risk of formation of bacterial charge and to increase the safety of the end product.

In the sector of liquid or semi-liquid food products, there are prior art machines for making liquid or semi-liquid food products (in particular soft ice cream) of the so-called "self-pasteurizing" type.

These machines are able to operate, without the need to remove the components for cleaning, for approximately 43 days.

For this reason, approximately every 43 days, the operator performs—after dismantling the components—a complete cleaning on these types of machines which is particularly long, that is, it requires a particularly lengthy time.

However, these machines are quite expensive (more expensive than so-called "standard" machines) as they are extremely complex.

In the relevant sector there are also "standard" machines for making liquid or semi-liquid food products (in particular soft ice cream), that is not of the "self-pasteurizing" type, which require frequent dismantling (daily) of the components, so as to ensure the necessary food safety of the product being made.

It should be noted that this type of machine requires a frequent dismantling of the components for the cleaning, which necessarily requires stopping the machine with a consequent loss of productivity.

For this reason, the operators feel the need to reduce the machine downtimes, that is, to reduce the unavailability of the machine.

The operators have therefore felt the need for a cleaning method which allows the machine downtimes to be reduced and which is simple and inexpensive.

SUMMARY OF THE INVENTION

The aim of this invention is therefore to provide a method for cleaning a machine for feeding liquid or semi-liquid products, in particular for soft ice cream, which meets the above-mentioned needs.

More specifically, the aim of this invention is to provide a method for cleaning a machine for feeding liquid or semi-liquid products which allows the machine downtimes to be reduced, that is, it reduces the unavailability of the machine.

The aim of this invention is to provide a method for cleaning a machine for feeding liquid or semi-liquid products which allows the quantity of cleaning fluids used to be reduced.

A further aim of this invention is to provide a method for cleaning a machine for feeding liquid or semi-liquid products which allows the number of components removed during the cleaning operations to be reduced.

According to the invention, these aims are achieved by a cleaning method which comprises the technical features set out in one or more of the appended claims.

BRIEF DESCRIPTION OF THE DRAWINGS

The technical features of the invention, with reference to the above aims, are clearly described in the claims below and its advantages are apparent from the detailed description which follows, with reference to the accompanying drawing which illustrates a non-limiting example embodiment of the invention and in which:

DESCRIPTION OF THE PREFERRED EMBODIMENTS

With reference to the accompanying drawings, the numeral 1 denotes a machine for making liquid or semi-liquid products, in particular for products of the soft ice cream or shake type.

Figure 1:
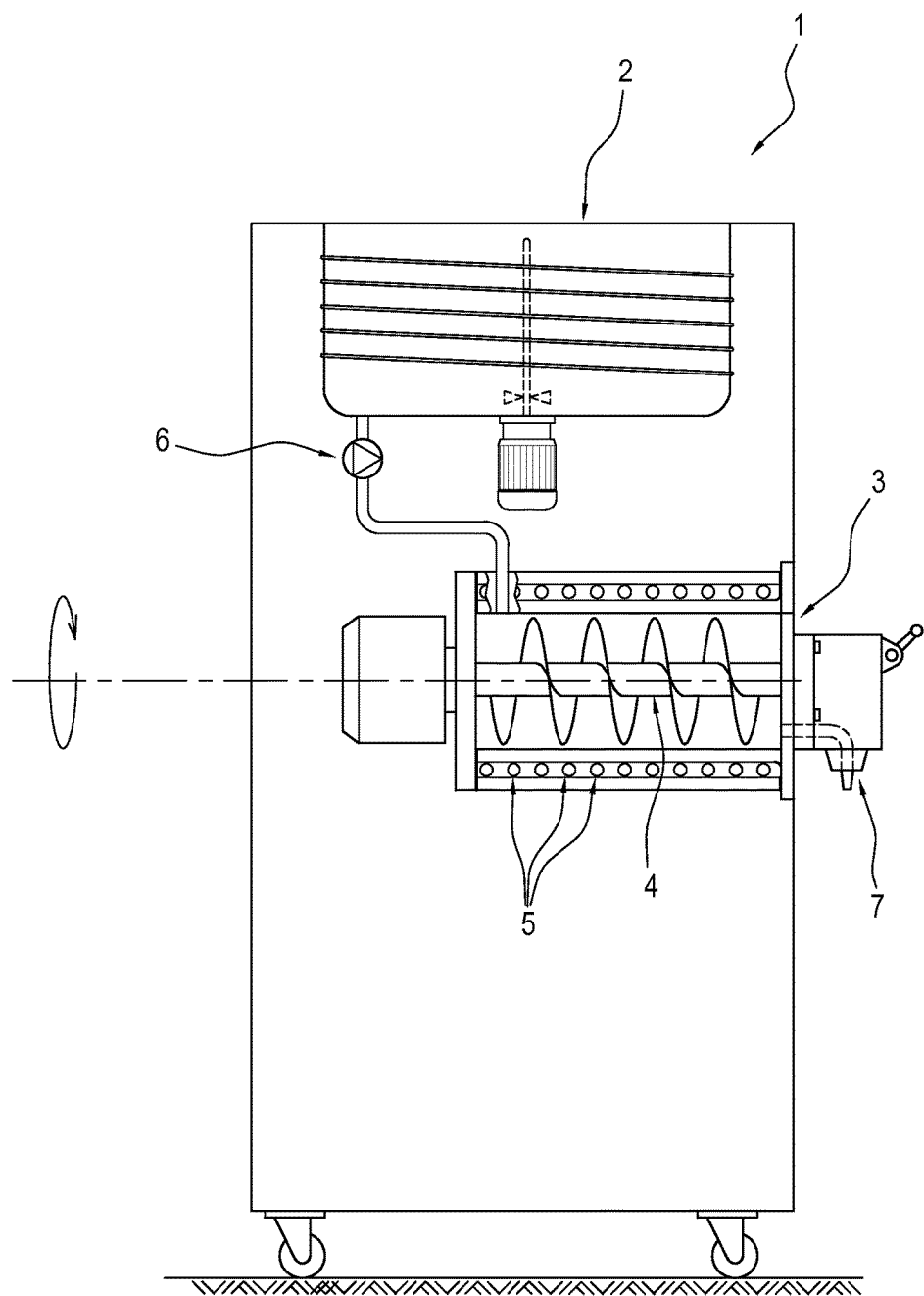
FIG. 1 is, by way of example, a schematic side view of a machine for making liquid or semi-liquid products wherein the cleaning method according to this invention is actuated.

It should be noted that the machine 1 is illustrated purely by way of example in FIG. 1.

The machine 1 illustrated in FIG. 1 comprises:

a first container 3 intended to contain a basic mixture or the finished product;

a second container 2 connectable to the first container 3 for feeding a basic mixture (which will be converted into finished product in the first container 3).

Preferably, according to the embodiment illustrated, the second container 2 is provided with a mixer and respective heat treatment means.

Moreover, the first container 3 is equipped with a mixer 4 designed to stir the basic mixture (or product) present inside the first container 3 for converting it into finished product.

Again, the first container 3 is equipped with means 5 for thermal treatment of the basic mixture, that is, of the product contained inside the container.

Preferably, the thermal treatment means 5 comprise a heat exchanger, designed for exchanging heat with the basic mixture, that is, the product contained inside the first container 3.

Preferably, the machine 1 comprises a dispensing device 7, connected to the first container 3 to allow the product contained in the first container 3 to be dispensed.

It should be noted that the machine 1 also comprises a thermal plant, configured to allow a cooling of the basic mixture or finished product inside the first container 3.

The thermal plant is operatively coupled to the heat treatment means 5.

Preferably, according to one embodiment, the thermal plant may also allow the heating of the basic mixture in the second container 2.

It should be noted that, preferably, the first container 3 is a mixing and cooling cylinder.

Preferably, the first container 3 is cylindrical and is equipped with a front opening for accessing the internal processing chamber.

On the other hand, the second container 2 is, in the embodiment illustrated, a tank 2.

Figure 2:
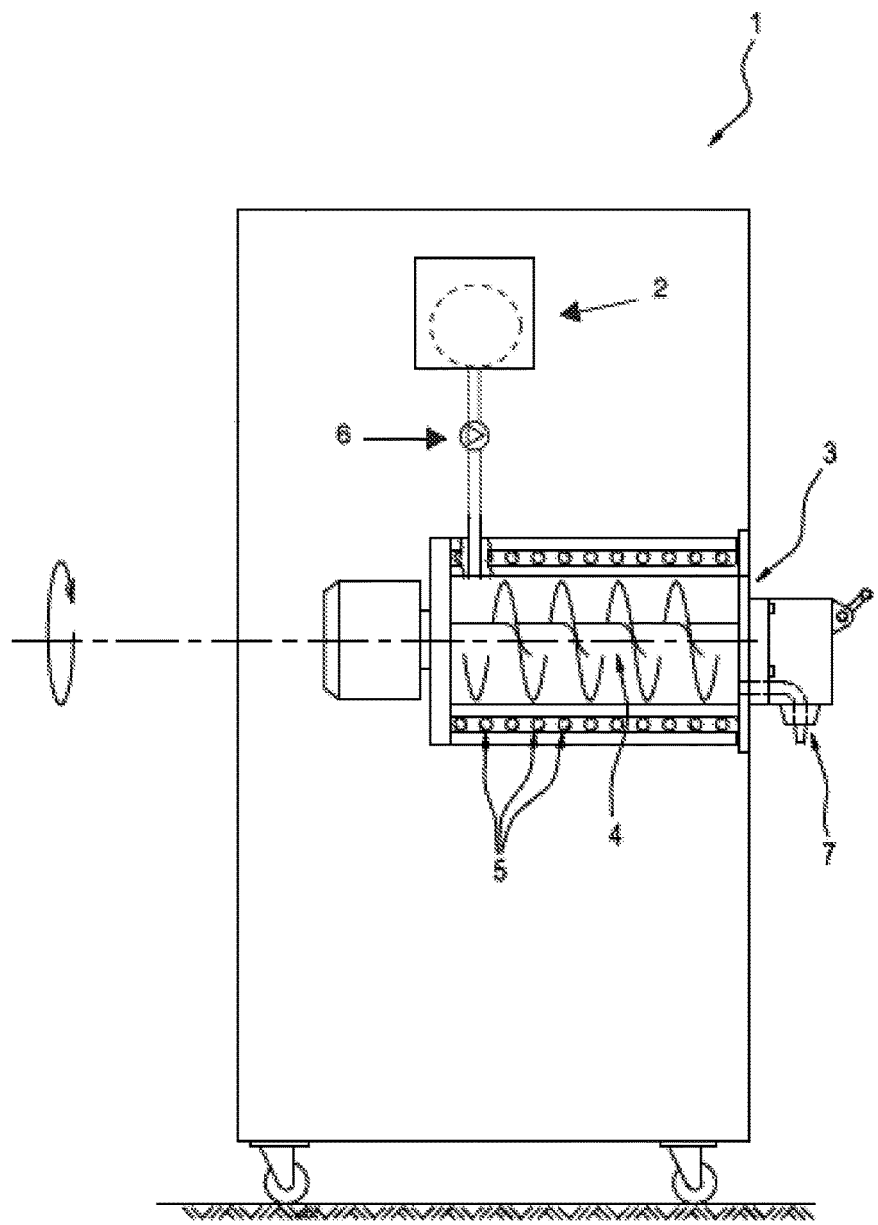
FIG. 2 is, by way of example, a schematic side view of an alternative machine for making liquid or semi-liquid products wherein the cleaning method according to this invention is actuated.

Alternatively, according to an embodiment shown in FIG. 2, the second container 2 is a container of a deformable type, preferably of the BIB type ("bag in box").

The BIB container contains the basic mixture and gradually deforms reducing the space occupied as the basic mixture is extracted.

It should be noted that the first and the second container are connected to each other, so that the mixture can be transferred, in use, from the second container 2 to the first container 3.

The method according to the invention relates to a method for cleaning the machine 1.

The method comprises the following steps:
a) emptying the basic mixture contained in the first container (3);
b) washing the first container (3) with a washing fluid;
c) at least partly filling the first container (3) with a cleaning fluid and subjecting the cleaning fluid in the first container (3) to a pasteurizing thermal treatment.

Preferably and advantageously, the pasteurizing thermal treatment is carried out by recirculating the cleaning fluid (that is to say, substantially continuously extracting and introducing the cleaning fluid).

Preferably, recirculation occurs by passing the cleaning fluid through a closed path including the first container 3. The recirculation allows, preferably, heating the cleaning fluid, that is, performing a so-called "recirculating pasteurizing."

Preferably, the cleaning fluid is water.

It should be noted that the pasteurizing of cleaning fluid means that the sanitizing action of the cleaning fluid is increased.

It should be noted that a cycle comprising the set of the steps from a) to c) is carried out, preferably, at a (each) predetermined time interval.

Preferably, the cycle comprising the steps from a) to c) is carried out at a (each) predetermined time interval of between 65 and 80 hours (yet more preferably between 65 and 75 hours).

Further, the cycle comprising the steps from a) to c) is carried out at a (each) predetermined time interval, less than 73 hours.

It should be noted that, advantageously, the fact of carrying out the cleaning cycle comprising the above-mentioned steps from a) to c) at a predetermined time interval means that machine downtimes are substantially reduced.

Moreover, advantageously, according to the cleaning method according to this invention a sanitizing fluid is not used, so that the food safety for the final operator is substantially increased.

In effect, the cleaning fluid, in particular the water, makes it possible to obtain a food safety which is greater than that of normal sanitizing fluids.

Experimental tests have shown that the cleaning method according to this invention is much faster than the methods of known type and moreover makes it possible to reduce the number of components to be removed.

The presence of the step c), wherein a cycle for pasteurizing the cleaning fluid is performed, allows the bacterial charge inside the machine to be further reduced.

The expression "pasteurizing cycle" means a heating thermal treatment of the product wherein the product is heated and kept at a first predetermined temperature (between 65° C. and 85° C.) for a predetermined time, followed by a subsequent cooling and maintaining at a second predetermined temperature (preferably approximately 4° C.).

More precisely, experimental tests have shown that in the majority of situations it is possible to clean the machine in less than half an hour.

Also, these tests have shown that the quantity of washing fluid and cleaning fluid required (including the water consumed) is considerably less than that of the prior art methods.

It should be noted that all the experimental tests have shown that, thanks to the particular sequence of steps of the method according to the invention, a perfect sanitization and hygiene of the machine is obtained, which guarantees excellent standards of safety.

Characteristic aspects of the cleaning method are described below in more detail.

The step b) of washing the first container 3 with washing fluid comprises a step of filling the first container 3 with the washing fluid.

Preferably, the washing fluid is water.

Preferably, the step of filling the first container 3 with the washing fluid comprises a step of introducing a quantity of water of between 2 and 55 liters, preferably five liters.

Preferably, the step b) comprises a step of brushing the surface of the first container 3.

Preferably, in the step b) there is a step of activating the mixer 4 inside the first container 3, for a predetermined time.

Further, in the step b) there is a step of emptying of the washing fluid from the first container 3.

It should be noted that the operations described above, for filling the first container 3 with a washing fluid, cleaning the first container 3 and emptying the washing fluid from the first container are performed, cyclically, for a predetermined number of times.

According to the method, the step c) of filling the first container 3 with a cleaning fluid (for example, water) and subjecting the water to a pasteurizing thermal treatment comprises a step c1) of heating the water inside the first container 3.

It should be noted that the pasteurizing thermal treatment comprises a heat treatment of the cleaning fluid (preferably there is a heating of the cleaning fluid).

Preferably, the heating of the cleaning fluid occurs at a temperature of between 60° C. and 85° C.

During the pasteurizing cycle, there is, preferably, a step of keeping the cleaning fluid at a predetermined temperature for a predetermined time.

Also, preferably, the step c) comprises a step C3) (preferably after the step c1) of cooling the cleaning fluid (that is, heated water) to a predetermined storage temperature (and preferably keeping the cleaning fluid at the above-mentioned predetermined temperature).

It should be noted that, advantageously, the method according to the invention allows the machine shutdowns to be reduced and also makes it possible to reduce the number of components to be removed.

Advantageously, the method ensures an optimum cleaning of the machine 1.

It should also be noted that, according to the invention, the use of fluids is substantially avoided.

Substantially, the cleaning is therefore optimized, reducing any food safety risks.

With reference to a machine 1 comprising a tank 2 and a cylinder 3, it should also be noted that, preferably, in the step b) there can be a step for activating a pump 6 for transferring the product from the second container 2 to the first container 3, for a predetermined time, for transferring the washing fluid from the second container 2 to the first container 3.

Further, the above-mentioned step c) may comprise a step c2) for activating, at predetermined time intervals and for a predetermined time, the pump 6 for transferring the product from the first container 3 to the second container 2 and the mixer 4 of the second container 2, to allow a recirculation of the cleaning fluid between the two containers 3, 2.

Again with reference to a machine 1 wherein there is a second container 2 of the type tank, the method comprises a further step of emptying the basic mixture contained in the second container 2 and a further step of washing the second container 2 with a washing fluid.

Further, in this case, the method comprises and a step of subjecting the cleaning fluid in the second container 2 to a pasteurizing thermal treatment.

The step of subjecting the cleaning fluid in the second container 2 to a pasteurizing thermal treatment comprises a step of recirculating the cleaning fluid contained in the second container 2, that is to say, by extracting from the second container 2 and introducing into second container 2, substantially continuously, the cleaning fluid.

In other words, the cleaning fluid removed from the second container 2 is made to pass through a closed circuit including the second container 2, so as to create a recirculation.

Further, again with reference to a machine 1 wherein there is a second container 2 of the tank type, the step of washing the first and second containers 3, 2 with a washing fluid comprises a step of at least partly transferring the washing fluid from the second container 2 to the first container 3.

Further, preferably, again with reference to a machine 1 wherein there is a second container 2 of the tank type, the method comprises a step of introducing the cleaning fluid in the second container 2 and transferring the cleaning fluid from the second container 2 to the first container 3 (it should be noted in this regard that the second container 2 is in connection with the first container 3).

According to a non-limiting example embodiment, the cleaning fluid is pasteurized both inside the second container 2 and inside the first container 3.

What is claimed is:

1. A cleaning method for a machine for processing liquid or semi-liquid products, comprising:
    providing a machine including a first container for containing a liquid or semi-liquid basic mixture or finished product; a system for thermal treatment of the liquid or semi-liquid basic mixture or finished product and a mixer,
    performing, in time sequence, the following steps:
    a) emptying the basic mixture or finished product contained in the first container;
    b) washing the first container with a non-pasteurizing washing fluid, including:
        a step of filling the first container with the washing fluid, and
        a step of emptying the washing fluid from the first container;
    c) at least partly filling the first container with a cleaning fluid and subjecting the cleaning fluid in the first container to a pasteurizing thermal treatment;
    performing the pasteurizing thermal treatment by recirculating the cleaning fluid contained in the first container by substantially continuously extracting the cleaning fluid from the first container and introducing the cleaning fluid into the first container, thereby making the cleaning fluid travel along a closed path including the first container;
    wherein the step c) comprises:
        heating the cleaning fluid in the first container;
        keeping the cleaning fluid heated in the first container to a pasteurization temperature for a predetermined time;
        cooling the cleaning fluid in the first container to a predetermined preservation temperature;
        maintaining the cleaning fluid in the first container at the predetermined preservation temperature;
    providing the machine with a second container containing a basic mixture and connectable to the first container for feeding basic mixture from the second container to the first container, the second container being deformable to reduce a space occupied by the second container as basic mixture is extracted from the second container;
    emptying the basic mixture contained in the second container;
    washing the second container with a washing fluid;
    at least partly filling the second container with a cleaning fluid;
    subjecting the cleaning fluid in the second container to a pasteurizing thermal treatment;
    providing that the machine includes a pump for transferring at least one chosen from washing fluid and cleaning fluid between the first container and the second container;
    wherein the step of washing the first container and the further step of washing the second container comprise a step of activating the pump to at least partly transfer washing fluid from the second container to the first container;
    recirculating cleaning fluid between the first container and the second container by activating the pump at predetermined time intervals to transfer cleaning fluid from the first container to the second container and vice versa, substantially continuously and along a closed path including the first container and the second container.

2. The cleaning method according to claim 1, wherein the cleaning fluid is water.

3. The cleaning method according to claim 1, and further comprising performing a cleaning cycle comprising a set of the steps from a) to c) at a predetermined time interval.

4. The cleaning method according to claim 3, wherein the predetermined time interval is between 65 and 80 hours.

5. The cleaning method according to claim 1, wherein the step b) of washing the first container with a washing fluid comprises a step of brushing the surface of the first container.

* * * * *